United States Patent
Skouboe et al.

(10) Patent No.: US 10,416,072 B2
(45) Date of Patent: Sep. 17, 2019

(54) PROBE FOR GAS SENSOR HAVING PURGE GAS PROTECTION

(71) Applicant: DANFOSS IXA A/S, Vejle (DK)

(72) Inventors: Allan Skouboe, Horsens (DK); Jesper Høyer, Vejle (DK); Carsten Moberg, Brenderup (DK)

(73) Assignee: Danfoss IXA A/S, Vejle (DK)

( * ) Notice: Subject to any disclaimer, the term of this patent is extended or adjusted under 35 U.S.C. 154(b) by 261 days.

(21) Appl. No.: 15/318,756

(22) PCT Filed: Jun. 17, 2015

(86) PCT No.: PCT/EP2015/063588
§ 371 (c)(1),
(2) Date: Dec. 14, 2016

(87) PCT Pub. No.: WO2015/193370
PCT Pub. Date: Dec. 23, 2015

(65) Prior Publication Data
US 2017/0131199 A1    May 11, 2017

(30) Foreign Application Priority Data

Jun. 19, 2014 (DK) .................................. 2014 00324

(51) Int. Cl.
*G01N 21/15* (2006.01)
*G01N 21/27* (2006.01)
*G01N 21/85* (2006.01)

(52) U.S. Cl.
CPC ............ *G01N 21/15* (2013.01); *G01N 21/274* (2013.01); *G01N 21/8507* (2013.01); *G01N 2021/8578* (2013.01); *G01N 2201/0233* (2013.01)

(58) Field of Classification Search
CPC .. G01N 21/15; G01N 21/274; G01N 21/8507; G01N 2201/0233; G01N 2021/8578
See application file for complete search history.

(56) References Cited

U.S. PATENT DOCUMENTS 5,353,629 A * 10/1994 Hunter .................. G01N 21/15
356/439
5,781,306 A * 7/1998 Hartig .................... G01N 21/31
250/373

(Continued)

FOREIGN PATENT DOCUMENTS

CA          984173 A       2/1976
CN       202829932 U       3/2013

(Continued)

OTHER PUBLICATIONS

International Search Report for PCT Serial No. PCT/EP2015/063588 dated Sep. 18, 2015.

*Primary Examiner* — Eric S. McCall
*Assistant Examiner* — Timothy P Graves
(74) *Attorney, Agent, or Firm* — McCormick, Paulding & Huber LLP

(57) ABSTRACT

A probe for an IR or UV sensor comprising a light emitter and detector is described comprising a lens. The detector detects the spectrums of the emitted light after it has passed a gas to be measured. The sensor of the present invention is especially suitable for such as harsh or aggressive environments measuring the exhaust gasses, for example in ships, vehicles, chimneys etc., and comprises purge gas protections for delicate optical parts to prevent particles etc. from the exhaust gas depositing on the optics. The sensor further has a flow of sample gas from the gas to be measured being adapted to prevent the purge gas from inferring with the measurements.

13 Claims, 4 Drawing Sheets

(56) References Cited

U.S. PATENT DOCUMENTS

| | | |
|---|---|---|
| 5,835,230 A | 11/1998 | McAndrew et al. |
| 2008/0283753 A1 | 11/2008 | Jensen et al. |
| 2012/0236323 A1 | 9/2012 | Knoppa |

FOREIGN PATENT DOCUMENTS

| | | | |
|---|---|---|---|
| DE | 10 2012 215 805 B3 | | 9/2013 |
| EP | 2388570 A1 | | 11/2011 |
| EP | 2 416 146 A2 | | 2/2012 |
| EP | 2 743 680 A1 | | 6/2014 |
| GB | 2274332 | * | 1/1993 |
| GB | 2 274 332 A | | 7/1994 |
| JP | S60233536 A | | 11/1985 |
| JP | 20122799 A | | 1/2012 |

* cited by examiner

PROBE FOR GAS SENSOR HAVING PURGE GAS PROTECTION

CROSS REFERENCE TO RELATED APPLICATION

This application is entitled to the benefit of and incorporates by reference subject matter disclosed in the International Patent Application No. PCT/EP2015/063588 filed on Jun. 17, 2015 and Danish Patent Application No. PA201400324 filed on Jun. 19, 2014.

TECHNICAL FIELD

A probe for an IR or UV sensor comprising a light emitter and detector is described comprising a lens. The detector detects the spectrums of the emitted light after it has passed a gas to be measured. The sensor of the present invention is especially suitable for such as harsh or aggressive environments measuring the exhaust gasses, for example in ships, vehicles, chimneys etc., and comprises purge gas protections for delicate optical parts to prevent particles etc. from the exhaust gas depositing on the optics. The sensor further has a flow of sample gas from the gas to be measured being adapted to prevent the purge gas from inferring with the measurements.

BACKGROUND

One example of gas sensor based on measuring the spectrum absorptions of emitted light by a gas is described in US 2008/0283753, wherein the pass band of a first filter is arranged within the pass band of a second filter and the evaluating device forms the difference of the signals and normalises it to the signal.

Using such a sensor in relatively harsh environments such as exhaust systems in ships, vehicles etc. will however expose the delicate parts environment within the exhaust stack that may comprise a wide range of particles and gasses that could damage them, or just reduce their lifetime. One option would be to protect the parts with sight glasses such that they becomes isolated from the harsh environment, but the transparency of these may then be reduced over time by settlement of particles etc.

Another example of a gas sensor is CA 984173 disclosing a photometer disclosing a probe with a mirror at the end such that light is passed down the probe to the mirror and is reflected back to the instruments of the device. The probe has many holes to allow free passage of the gasses and air lines to purge the probe and for calibrating. The purge gasses enter from an externally positioned section covering holes for the purge gas to be feed into the measuring region. An disadvantage with the this construction is e.g. the free passage of gasses to the measuring region making it hard to empty the measuring region from gasses during calibration as it would require a significant pressure to overcome the forces of pressure from the freely flowing gasses.

Another example is DE 10 2012 215 805 showing a split system where two parts of the sensor is positioned at opposite sides of the gas containing region making it even more impossible to empty the measuring region (being the gas containing region) from gasses during a possible calibration.

SUMMARY

The present invention introduces a probe overcoming such problems.

The present invention relate to a gas sensor comprising a probe with light path for directing emitted light through a first purge gas volume and a measuring region, where the probe is adapted for a purge gas to flow in the first purge gas volume and a sample gas to flow through the measuring region, and where gas to be measured present in the measuring region is prevented from entering the first purge gas volume by the purge gas flowing in a direction towards the measuring region. By positioning delicate parts (thus as but not limited to optical parts) such that they are separated from the measuring region by the first purge gas volume, the flow of purge gas prevents the gas from the measuring region to reach the delicate pats.

To ensure there is no direct of the measuring region to the gas containing environment, such that harsh environment such that the flow conditions etc. is controllable and, enabling a regulation of the respective flows of gas to the measuring region, either to make them uniform, or to make some or all of them different, the probe comprises a sample inlet being in flow communication with the flow of gas to be measured, and where this sample inlet is in flow communication with a sample gas conduit and where sample inlet is positioned such that the flow of gas to be measured does not tend unguided to flow into the sample inlet. The sample inlet thus is not positioned in the direction of the flow of gas to be measured, but rather the sample gas enters the probe from the sample inlet in a transverse direction with an angle compared to the flow direction of the gas to be measured being higher than or equal to about 45 degrees.

Since it often is required to calibrate the sensor the present invention takes advantage of the purge gas already present using this as calibration gas, and the sensor accordingly is capable to operate in a operation mode and a calibration mode, where sample gas only passes the measuring region in the operation mode, but the purge gas flows both in the operation and calibration modes.

The sensor may comprise a second purge gas volume similar to the first and protecting further delicate parts, or even further purge gas volumes depending on the number of delicate parts and their positions such as relative to the light path.

To ensure a uniform distribution of the purge gas and thus a turbulent free flow in the purge gas volume(s) the probe comprises a supply path(s) for feeding purge gas to the purge gas volume(s), where the supply path(s) comprises a encircling section surrounding the first purge gas volume(s) having a point inlet situated in the end close to the measuring region wherefrom the purge gas spreads to the full circumference of the encircling section and enters the purge gas volume(s) in the end distal to the measuring region.

When in the calibration mode to empty the measuring region for gas disturbing the calibration measurements, the calibration mode includes closing for the sample gas entering the measuring region, letting the purge gas flow for a given time period of time to empty the measuring region of sample gas and then making calibration measurements.

To prevent gas from the environment being measured from entering the probe during calibration the flow of purge gas usually forms a sufficient barrier, but in one embodiment to the flow of purge gas is increased during calibration mode, thus improving this protection.

To ensure a clean and dry purge gas the purge gas are dried and optionally filtered before entering the first and second encircling paths, thus removing moist and other elements that might affect the calibration measurements.

DETAILED DESCRIPTION

Figure 1:
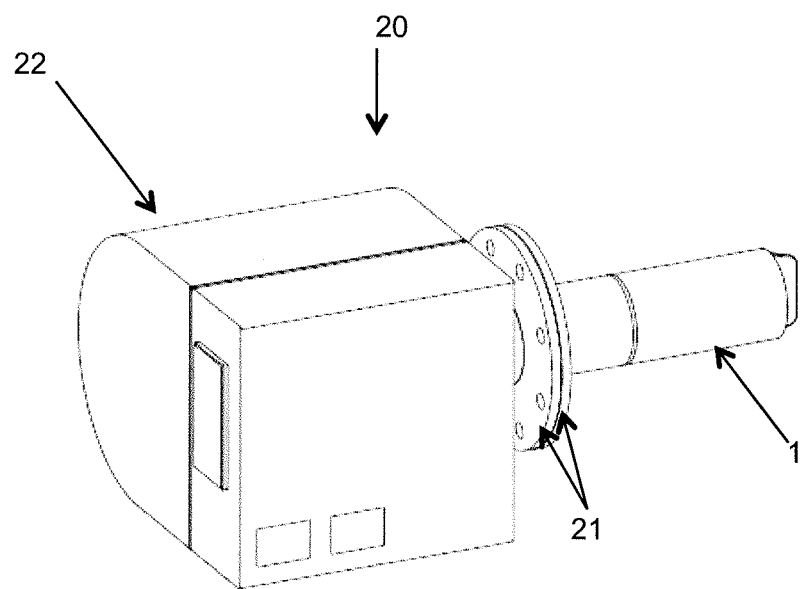
FIG. 1 Sensor according to the present invention comprising a back-end and a probe.

FIG. 1 shows an external view of a sensor (20) with a back-end (22) and a probe (1) according to the present invention where the probe part (1) is adapted to be inserted in connection with e.g. an exhaust gas. The probe (1) is attached to the sensor (20) by flanges (21) of the probe (1) and sensor (20) respectively having openings where nuts and bolts may be used to fix the two parts together. Any other means to attach the parts would however also apply to the present invention.

Figure 2:
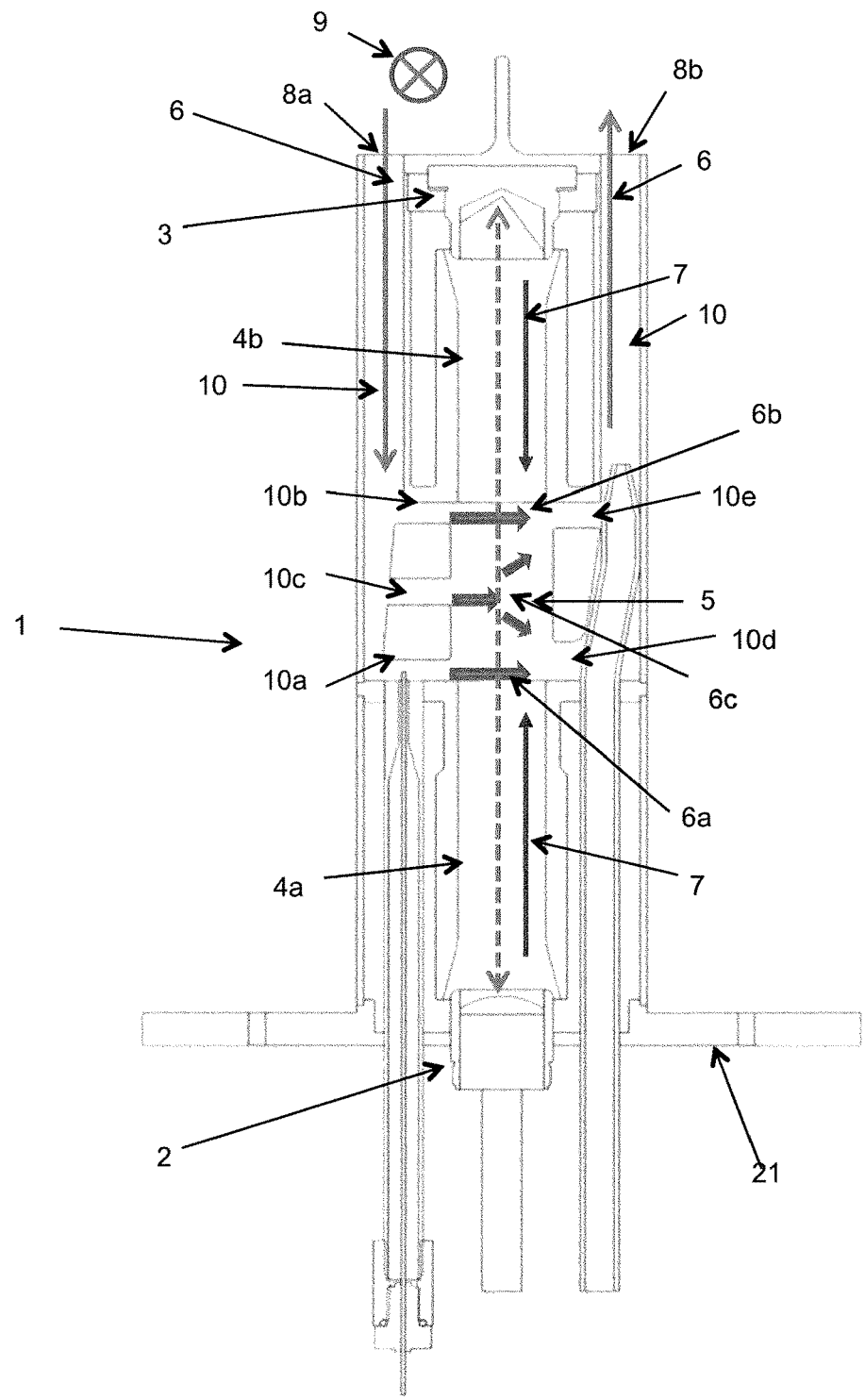
FIG. 2 Illustration of an embodiment of an aspect of a probe for a gas sensor showing the light path passing a first and second purge gas volume.

FIG. 2 shows a top view of an embodiment of the probe (1) according to the present invention.

The probe (1) comprises a light source and detector system positioned in connection to a lens (2). The detector emits light through the lens (2) towards a reflector (3) by a light path illustrated by the dashed arrow reaching from the lens (2) to the reflector (3), where it is reflected back towards and back through the lens (2) to a detector. The detector and light source is not illustrated. The emitted light passes through a first purge gas volume (4a), a measuring region (5) and a second purge gas volume (4b).

The first (4a) and second (4b) purge gas volumes are positioned between the measuring region (5) and respectively the lens (2) and the reflector (3). Purge gas (7) flows in each of the purge gas volumes (4a, 4b) in the direction towards the measuring region (5) thus preventing gas or other substances and particles in the measuring region (5) from entering into the purge gas volumes (4a, 4b) by the flow of purge gas, this thus forming a protection or curtain for respectively the lens (2) and reflector (3). The purge gas (7) thus flows essentially in directions parallel to the light path, at least in the areas of the purge gas volumes (4a, 4b).

In some embodiment of the present invention the probe (1) comprises none or only one of the first (4a) and second (4b) purge gas volumes.

The purge gas (7) could be a specific gas or just air (e.g. being filtered or cleaned) conveyed into the system.

The probe (1) comprises a sample inlet (8a) being in flow communication with the flow of gas (9) to be measured, and where this sample inlet (8a) is in flow communication with a sample gas conduit (10) being connected to the measuring region (5) by three branches (10a, 10b, 10c). Each of the branches in one embodiment has different flow restrictions, or alternatively as in the illustrated embodiment, the sample gas conduit (10) changes flow restriction in the sections between the branches (10a, 10b, 10c). The sample gas (6) entering the sample inlet (8a) (such as being dragged into the sample inlet (8a) from the flow of gas (9) by e.g. a venturi pump) is by the branches (10a, 10b, 10c) splits into three flows entering the measuring region (5). With different flow restrictions in the branches (10a, 10b, 10c) it is possible to regulate the individual three flows rates (6a, 6b, 6c) such that they are the same or alternatively so that two or all of them are different.

In the illustrated embodiment the branches (10a, 10b, 10c) formed by two 'flow guides' positioned as walls between the sample gas conduit (10) and the measuring region (5), and where the different flow restrictions are formed by a slope of the walls of these 'flow guides' directing towards the sample gas conduit (10) thus changing its cross section area and thereby the flow restriction. Alternative embodiments could be introduced such as inserting glass capillary tubes of different lengths and/or internal diameters.

The illustrated embodiment shows three branches (10a, 10b, 10c) splitting the sample gas (6) into three flows (6a, 6b, 6c), but an alternative embodiment only comprises two flows (6a, 6b) and two branches (10a, 10b). In this embodiment the first flow (6a) enters the measuring chamber (5) in the area close to the first purge gas volume (4a) and the second flow (6b) in the area close to the second purge gas volume (4b) and are in this manner adapted to remove purge gas (7) entering the measuring region (5) from the first (4a) and second (4b) purge gas volume respectively, especially from a middle region of the measuring region (5) such that this middle region comprises sample gas (6) un-mixed with purge gas (7). If the sample gas (6) was mixed with the purge gas (7) its concentration would be altered and thus the measurements affected. It has however been found often to be difficult filling the middle region with sample gas (6) having only the first and second flows (6a, 6b) and therefore to this purpose in the illustrated embodiment of the present invention a third branch (10c) is introduced forming a third flow (6c) feeding the middle region.

A sample outlet (8b) for expelling the sample gas (6) from the probe (1) after it has left the measuring region (5) and where said sample outlet (8b) is positioned in flow communication with the flow of gas (9) to be measured.

The measuring region (5) is connected to the sample outlet (8b) through at least two outlets branches (10d, 10e) of the section of the sample gas conduit (10) connecting the measuring region (5) to the sample outlet (8b). In the preferred there are only two outlet branches (10, 10e) to guide the flows (6a, 6b, 6c) correctly through the measuring region (5) to fill it. In other configurations it has been found by simulations that undesired turbulences may be formed preventing the sample gas (6) from filling the measuring region (5), especially its middle region.

The sample gas (6) as it enters the sample gas conduit (10) is directed into the measuring region (5) as three flows (6a, 6b, 6c) that may have similar or different flow rates. The inlet outlet regions of the measuring region (5) are each connected to a separate outlet branch (10d, 10e) such that the first flow (6a) and second flow (6b) passes, or transverses, the measuring region (5) with an angle relative to the direction of the light path and/or the flow of the purge gas (7) being higher than 45 degrees, or more specifically higher than 60 degrees or more specifically in the area around 90 degrees thus being essentially perpendicular thereto. The first (6a) and third (6c) flows in their flow from the respective branches (10a, 10c) to the respective outlet branches (10d, 10e) will drag the entering purge gas (7) along and out of the measuring region (5) thereby preventing it from getting in contact with the middle region and the second flow (6b) inferring with the measurements.

In the same manner the second flow (6b) transverses the measuring region (5) at an angle relative to the direction of the light path and/or the flow of the purge gas (7) being higher than 45 degrees, or more specifically higher than 60 degrees or more specifically in the area around 90 degrees thus being essentially perpendicular thereto, but where this may change as it passes as it may leave the measuring region (5) through one or both of the outlet branches (10b, 10e) also being used by the first (6a) and third (6c) flows. Preferably it enters the measuring region (5) by an angle in the range around 90 degrees.

The probe (1) in the illustrated embodiment is positioned in connection with the flow of gas (9) in a manner where sample inlet (8a) is at an angle relative to the flow direction of the gas (9) to be measured being higher than 45 degrees, or more specifically higher than 60 degrees or more specifically in the area around 90 degrees thus being essentially perpendicular thereto. The same applies to the sample outlet (8b). Further, the sample gas (6) enters the probe (1) from a sample inlet (8a) positioned behind the reflector (3) seen in the direction of the emitted light from the lens (2).

Introducing a sample inlet (8a) in a manner where it is positioned with an angle to the flow of gas such as close to 90 degrees it is ensured the gas does not itself tend to flow into the probe (1) but is dragged into the sample inlet (8a) e.g. by a venturi pump whereby it is it is possible to control the flowrates within the probe (1). This is unlike e.g. EP 2 604 999 where the inlets are positioned in the flow path of the gas such that it enters directly into the probe. By dragging the gas into the sample inlet (8a) the exchange rate of sample gas (6) within the measuring region (5) will be well known and defined just as it eases the task of emptying the measuring region (5) for calibration as to be described below.

To avoid mixing the sample gas (6) expelled from the sample outlet (8b) with the sample gas (6) entering the sample inlet (8a), an extension (11) is positioned between the sample inlet (8a) and sample outlet (8b) reaching out from the probe (1) into the flow of the gas (9).

Figure 3:
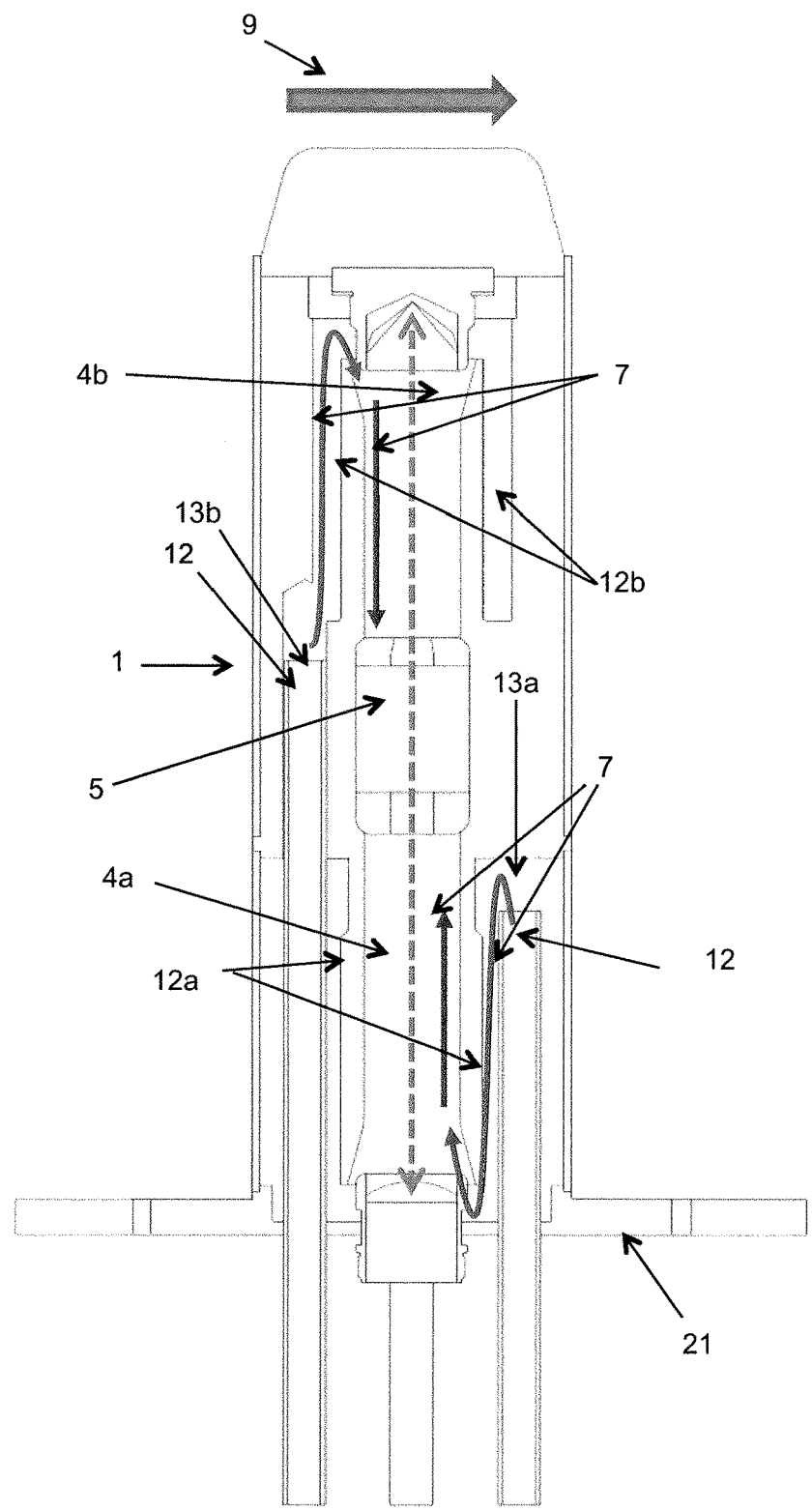
FIG. 3 Illustration of an embodiment of a second aspect of a probe for a gas sensor showing a purge gas supply path first and second purge gas volumes.

FIG. 3 shows a further feature of the present probe (1) showing it in a top-view and having a supply path (12) of purge gas (7) to the first purge gas volume (4a) comprises a first encircling section (12a) surrounding the first purge gas volume (4a) having a point inlet (13a) situated in the end close to the measuring region (5), thus distal to the lens (2), wherefrom the purge gas spreads to the full circumference of said first encircling section (12a) and enters said first purge gas volume (4a) in the end close to the lens (2). The encircling section (12b) may be formed as one coaxial chamber to the first purge gas volume (4a) or as a number of individual conduits extending from the supply path (12) to inlets to the first purge gas volume (4a) situated in the end proximal to the lens (2). In the present context 'point inlet' is to be understood in the sense that the flow path (12) changes from being narrow, cross section area is significantly smaller than the cross section area of e.g. the first purge gas volume (4a), but it spreads into an substantially wider first encircling section (12a) having cross section area larger than that of e.g. the first purge gas volume (4b).

Figure 4:
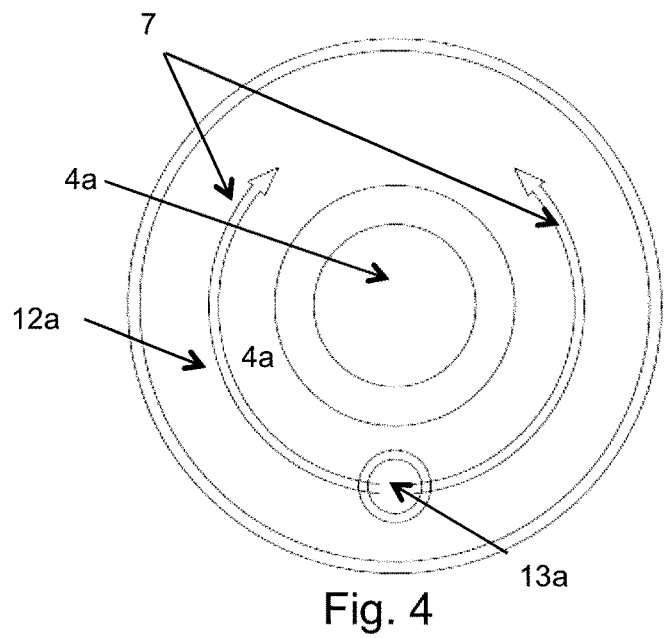
FIG. 4 Illustration of a purge gas supply path encircling a purge gas volume from a point like inlet.

FIG. 4 shows a cross section view of the encircling section (12a) at the point inlet (13a) with the purge gas (7) spreading from the supply path (12) through the point inlet (13a) having a cross section area smaller than that of the encircling section (12a) and purge gas volume (4a).

Figure 5:
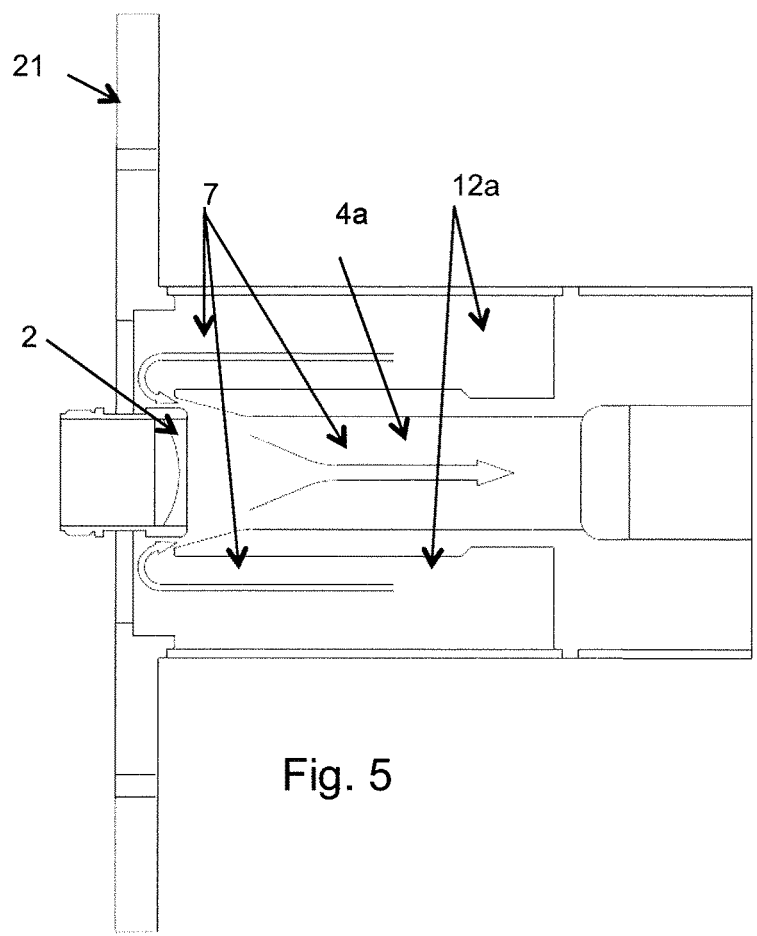
FIG. 5. Illustration of the encircling purge gas supply path showing the purge gas entering at a position close to the measuring region and entering the purge gas volume at a position distal to the measuring region.

FIG. 5 shows a top view of the section around the lens (2) showing the purge gas (7) entering from the encircling section (12a) to the purge gas volume (4a) in a substantially uniform manner around the circumference of the lens (2) forming a laminar flow in the purge gas volume (4a).

In the same manner and formed similar or differently to the first encircling section (12a), the present probe (1) may comprise a supply path (12) of purge gas (7) to the second purge gas volume (4b) that comprises a second encircling section (12b) surrounding the second purge gas volume (4b) and having a point inlet (13b) situated in the end close to the measuring region (5), thus distal to the reflector (3), wherefrom the purge gas spreads to the full circumference of said second encircling section (12b) and enters said second purge gas volume (4b) in the end close to the reflector (3).

The setup having the point inlets (13a, 13b) positioned at a distance relative to the lens (2) and reflector (3) respectively and then spreading in a circumference manner around the first and second purge gas volumes (4a, 4b) helps distributing the entering purge gas (7) uniformly in the circumference of the lens (2) and reflector (3), otherwise there would be differences in the incoming purge gas (7) inside the purge gas volumes (4a, 4b) thus forming turbulences that might actually help particles in entering from measuring region (5) into the purge gas volumes (4a, 4b), rather than preventing it.

The present probe (1) further is capable to operate in an operation mode and a calibration mode. The sample gas (6) only flows in the operation mode whereas the purge gas (7) flows both in the operation and calibration modes, where it operates as purge gas (7) during the operation mode according to the previous description, but is being used as calibration gas in the calibration mode, where the sample gas (6) flow is closed.

To prevent gas (9) from entering the system during calibration mode it has been found sufficient maintaining or increasing the flow of purge gas (7) in the system. In this manner purge gas (7) are conveyed out of the sample inlet (8a) and sample outlet (8b) in the direction against the gas (9) thus expelling the gas (9) before into the system by sample inlet (8a) and sample outlet (8b). Purge gas (7) is also conveyed out of the sample outlet (8b) during normal operation as also described above, but prevented from entering the part of the sample gas conduit (10) connected to the sample inlet (8a) by a valve or other means, or simply by the flow of sample gas (6) in the system.

The calibration mode includes closing for the sample gas (6) entering the measuring region (5) letting the purge gas flow for a given time period of time to empty the measuring region (5) of sample gas (6) and then making calibration measurements. The purge gas (7) is therefore of a known composition having a well-defined and known absorption spectrum, and may in one embodiment dried before entering the supply paths (12) to ensure it is clean of particles and moist that might influence the calibration measurements.

As also described above, due to the position of the sample inlet (8a) and that the sample gas (6) is dragged into the probe (1) and directed to the measuring region (5) rather than flowing directly into it, all flows within the probe (1) is controllable and it does not require to counter act the forces of the gas to keep it out as in the cases of the probes where there is direct gas access to the measuring region.

While the present disclosure has been illustrated and described with respect to a particular embodiment thereof, it should be appreciated by those of ordinary skill in the art that various modifications to this disclosure may be made without departing from the spirit and scope of the present disclosure.

What is claimed is:

1. A gas sensor comprising a probe comprising within a light path for directing emitted light through a first purge gas volume and a measuring region, where the probe is adapted for a purge gas to flow in a first purge gas volume and a sample gas to flow through the measuring region, wherein the purge gas flows in a direction towards the measuring region and the sample gas enters the probe through a sample inlet being in flow communication with a flow of gas to be measured, and where this sample inlet is in flow communication with a sample gas conduit communicating the sample gas to the measuring region, wherein said sample inlet is positioned such that the sample gas enters the probe in a transverse direction with an angle compared to the flow direction of the gas to be measured being higher than or equal to 45 degrees, wherein the probe comprises a detector configured to detect spectrums of emitted light passing through the sample gas in the measuring region, and wherein the flow direction of the gas to be measured is transverse to a direction of the light path such that an angle formed between the flow direction of the gas to be measured and the direction of the light path is higher than or equal to 45 degrees.

2. The probe according to claim 1, wherein said sample inlet is positioned such that the sample gas enters the probe in a transverse direction with an angle compared to the flow direction of the gas to be measured being around 90 degrees.

3. The gas sensor according to claim 1, where the sensor can operate in a operation mode and a calibration mode, where sample gas only passes the measuring region in the operation mode, but the purge gas flows both in the operation and calibration modes, thus being used as calibration gas.

4. The gas sensor according to claim 3, wherein the probe comprises a second purge gas volume and where the probe is adapted for a purge gas to flow in the second purge gas volume in a direction towards the measuring region and where the light path passes the second purge gas volume, and where the second purge gas volume is positioned between the measuring region and a reflector.

5. The gas sensor according to claim 3, where the probe comprises a supply path for feeding purge gas to the first purge gas volume, where the supply path comprises a first encircling section surrounding the first purge gas volume having a point inlet situated in the end adjacent to the measuring region wherefrom the purge gas spreads to the full circumference of said first encircling section and enters said first purge gas volume in the end distal to the measuring region.

6. The gas sensor according to claim 5, where a lens is situated in connection to the first purge gas volume such that said first purge gas volume is positioned between said lens and said measuring region.

7. The gas sensor according to claim 5, where the probe comprises a supply path for feeding purge gas to the second purge gas volume, where the supply path comprises a second encircling section surrounding the second purge gas volume having a point inlet situated in the end adjacent to the measuring region wherefrom the purge gas spreads to the full circumference of said second encircling section and enters said second purge gas volume in the end distal to the measuring region.

8. The gas sensor according to claim 1, where the gas sensor is configured to, during a calibration mode, prevent sample gas from entering the measuring region, let the purge gas flow for a given time period of time to empty the measuring region of sample gas and then make calibration measurements.

9. The gas sensor according to claim 8, where the flow of sample gas is induced by a venturi pump and where said venturi pump is closed during calibration mode.

10. The gas sensor according to claim 8, where the flow of purge gas is increased during calibration mode.

11. The gas sensor according to claim 2, where the sensor can operate in a operation mode and a calibration mode, where sample gas only passes the measuring region in the operation mode, but the purge gas flows both in the operation and calibration modes, thus being used as calibration gas.

12. The gas sensor according to claim 4, where the probe comprises a supply path for feeding purge gas to the first purge gas volume, where the supply path comprises a first encircling section surrounding the first purge gas volume having a point inlet situated in the end adjacent to the measuring region wherefrom the purge gas spreads to the full circumference of said first encircling section and enters said first purge gas volume in the end distal to the measuring region.

13. The gas sensor according to claim 1, the angle formed between the flow direction of the gas to be measured and the direction of the light path is 90 degrees.

* * * * *